United States Patent
Ehwald et al.

(10) Patent No.: US 7,284,413 B2
(45) Date of Patent: Oct. 23, 2007

(54) METHOD AND APPARATUS FOR MEASURING VISCOSITY

(76) Inventors: Rudolf Ehwald, Strelitzer Strasse 6, D-10115 Berlin (DE); Karl-Ernst Ehwald, Pflaumenallee 17, D-15234 Frankfurt/Oder (DE); Dieter Knoll, Uferstrasse 7, D-15230 Frankfurt/Oder (DE); Wolfgang Winkler, Pflaumenallee 50, D-15234 Frankfurt/Oder (DE); Henning Zinke, Wildbahn 64, D-15236 Frankfurt/Oder (DE)

(*) Notice: Subject to any disclaimer, the term of this patent is extended or adjusted under 35 U.S.C. 154(b) by 0 days.

(21) Appl. No.: 09/865,338

(22) Filed: May 28, 2001

(65) Prior Publication Data

US 2001/0045122 A1  Nov. 29, 2001

(30) Foreign Application Priority Data

May 26, 2000  (DE) ................. 100 27 684

(51) Int. Cl.
*G01N 11/10* (2006.01)
(52) U.S. Cl. .................... 73/54.23; 73/54.24
(58) Field of Classification Search .......... 73/54.23, 73/54.24, 54.25, 54.26, 54.27
See application file for complete search history.

(56) References Cited

U.S. PATENT DOCUMENTS 6,210,326 B1 * 4/2001 Ehwald ................. 600/365
6,267,002 B1 * 7/2001 Ehwald et al. ........... 73/54.01
6,269,685 B1 * 8/2001 Oden ..................... 73/54.17
6,311,549 B1 * 11/2001 Thundat et al. .......... 73/54.24

FOREIGN PATENT DOCUMENTS

| DE | 44 46 695 | 6/1996 |
|----|-----------|--------|
| DE | 195 01 159 A1 | 7/1996 |
| DE | 197 14 087 A1 | 10/1998 |
| DE | 198 04 326 A1 | 8/1999 |
| DE | 198 06 905 A1 | 9/1999 |

OTHER PUBLICATIONS

Ehwald et al.: Viscosimetric Affinity Assay; Analytical Biochemistry 234, pp. 1-8 (1996).
Kulicke, W.M. et al.: Experimentell Techniken (Rheometrie) und Stabilitaetskriterien; Excerpt from Fliessverhalten von Stoffgemischen; (Huethig Wepf. publ. Basel, Heidelberg, New York, 1996).
Beyer et al.: Viskosimetrische Affinitaetssensoren; Lebensmittel- & Biotechnologie Apr. 1996.

* cited by examiner

*Primary Examiner*—Daniel S. Larkin
(74) *Attorney, Agent, or Firm*—Gudrun E. Huckett

(57) ABSTRACT

An apparatus for measuring the viscosity of a fluid having a first rigid member extending from a body of semiconductor material and provided with a first conductive path and a second resiliently flexible member provided with a second conductive path and arranged in cantilever fashion over the rigid member. At least one of the conductive paths may be selectively energized to brig about relative movement between the rigid and flexible member. Subsequent deenergization of the path causes the resiliently flexible member to return to its initial position, the rate of return being measured to derive a signal representative of the viscosity. Also described are methods of carrying out the measurement and of fabricating the apparatus.

30 Claims, 2 Drawing Sheets

METHOD AND APPARATUS FOR MEASURING VISCOSITY

BACKGROUND OF THE INVENTION

1. Field of the Invention

Figure 1:
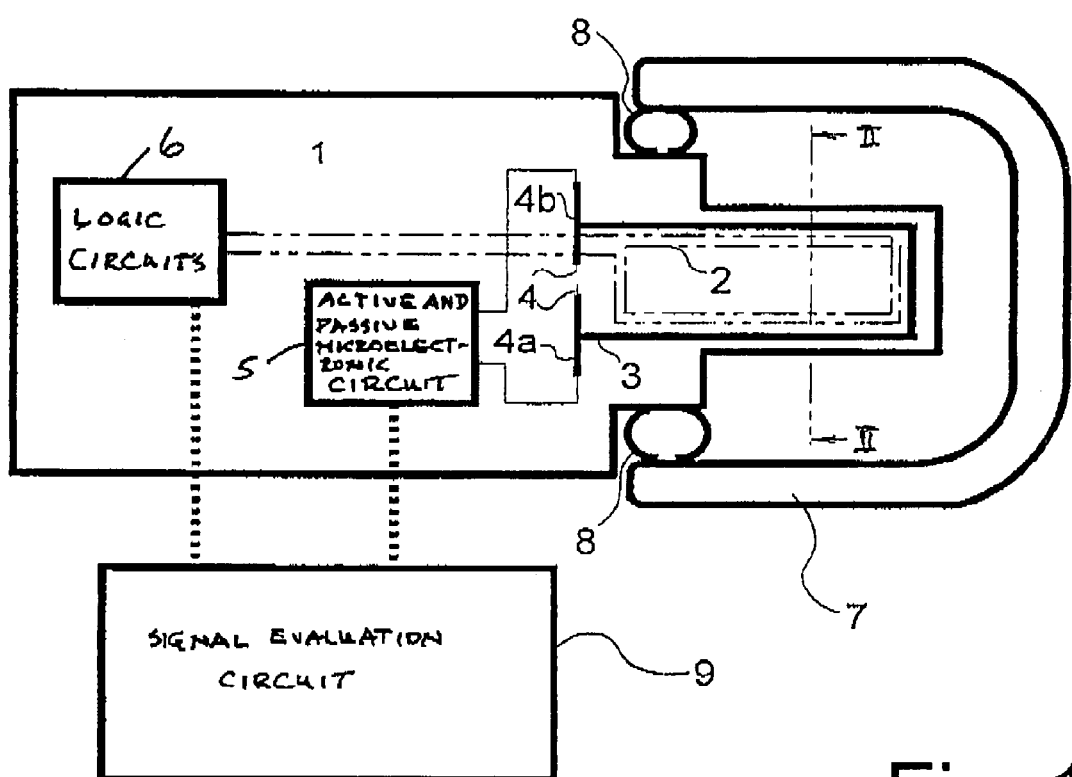

The invention, in general, relates to a method of, and to an apparatus for, measuring viscosity and, more particularly, to the viscometric measurement of minute quantities of fluid substances.

2. The Prior Art

The viscometric observation of the activity of hydrolytic enzymes, the speed of polymeric synthesis, the course of clotting or coagulation processes and of other biotechnologically important processes is well-known. However, measurements with conventionally used viscometers, such as, e.g. rotation viscometers or capillary viscometers, usually require relatively large quantities of fluid. As described by W. M. Kulicke in Flowing Behavior of Substances and Substance Mixtures (Hüthig Wepf. publ. Basel, Heidelberg, New York, 1986), samples of the fluids are removed from their environment and transferred to the measuring device.

Yet for many tasks in polymer chemistry, biochemistry and physiology there exists, particularly in connection with highly viscous fluids, a demand for a viscosity measuring probe capable of analyzing quantities in the range of micro liters, for instance, on micro titer panels, within short intervals and without noticeably affecting the volume of the sample or environment. Miniaturization is particularly important in the context of the development of implantable or semi-invasive viscometric affinity sensors. Such sensors are based on a combination of viscometric affinity essay and micro dialysis, and they make it possible continuously to measure the concentration of glucose in a physiological system; see, for instance, Ehwald, R., Ballerstädt, Dautzenberg in Anal. Biochem. 234, 1-8; 1996, and Beyer, P. U., Ballerstädt, R., Ehwald, R., Grocer. biotechnol. 13, 143-146, 1996, where the viscosity of a sensitive fluid within the dialysis fiber serves as the measuring parameter. In the disclosed viscometric glucose sensor, the sensitive fluid is a concentrated solution of dextran molecules cross-linked by affinity bonding with the tetravalent glucose-binding lectin concanavalin A (ConA). Glucose diffusing from the exterior into the dialysis fiber lumen displaces the terminal glucose units of the cross-linked dextran molecules from their affinity bonding with the lectin and decreases the viscosity of the sensitive fluid as a function of the concentration; see Beyer, P. U., Ballerstädt, R., Ehwald, R., Lebensm. Biotechnol. 13, 143-146, 1996.

An implantable micro sensor for the subcutaneous determination of glucose based on affinity viscometry is disclosed by German patent specification 195 01 159 A1. In that micro sensor, a hollow fiber for the dialysis and a measuring system are hydraulically connected to an enclosed completely fluid-filled flow system. The measuring system is provided with a micro engine for moving the sensitive fluid and with a pressure, volume or flow sensitive transducer.

A further viscometric affinity sensor is known from German patent specification 197 14 087 A1, in which the diffusion of analyte and the measurement of viscosity are sequentially carried out at different locations. The sensor requires the sensitive fluid to flow through a hollow fiber segment serving as a dialysis chamber at a viscosity which is strongly dependent on the analyte. The viscosity of the sensitive fluid exiting from the segment after modification by the diffusible analyte constitutes a measure of the concentration of the analyte in the vicinity of the segment.

The processes of measuring viscosity changes in a dialysis hollow fiber segment are based upon either measuring the flow resistance of the sensitive fluid in the hollow fiber segment itself (German patent specification 195 01 159 A1) or in a capillary positioned downstream from the hollow fiber segment (German patent specification 197 14 087 A1). Since these processes require a pumping device and a viscosity measuring device located outside of the dialysis hollow fiber, the sensitive fluid in the dialysis fiber segment is, in the known viscometric affinity sensors, hydraulically connected to a fluid volume remote from the segment. In such sensors, it is necessary by special structural measures to prevent, or at least limit, the diffusive exchange with a dead volume of the sensitive fluid in order to avoid undefined delays in signal generation. In accordance with German patent specification 197 14 087 A1, this is accomplished by a constant resupply of fresh sensitive fluid from a reservoir. It is, however, unlikely that such a system may be realized in an implanted sensor.

Furthermore, a sensor for measuring viscosity and density is known from German patent specification 198 04 326 A1. The sensor is provided with a flexible tongue made from silicon nitride, silicon oxide, a metal or from a compound material, and with an oscillator mechanically coupled to the flexible tongue for imparting oscillations to it. The measuring medium is analyzed by evaluating the oscillations. Such and similar sensors based upon the attenuation of oscillations (e.g. German Patent specification 198 06 905) cannot, however, be applied to measuring the viscosity of small quantities of highly viscous fluids in which no oscillations can be generated because of the extremely high attenuation.

Other known or obvious possibilities of measuring the viscosity in very small fluid volumes, such as, for instance, an optical analysis of Brownian particle movement, electrophoresis or dielectrophoresis, may not easily be applied to highly viscous polymeric solutions of an undefined electrolyte composition.

Hitherto, no apparatus adaptable to miniaturization and cost efficient fabrication has become known which is suitable for taking precise measurements of high viscosities in a very small and static measuring zone, such as, for example, a dialysis chamber, and for converting such measurements into electrical signals.

OBJECTS OF THE INVENTION

It is a general object of the invention to provide a method and an apparatus for measuring the viscosity of very small quantities of fluid.

Another object of the invention resides in the provision of a method and an apparatus for measuring the viscosity of very small amounts of very highly viscous fluids.

Still another object of the invention is to provide for a method and an apparatus for in situ measuring very small quantities of very highly viscous fluids.

Yet another object of the invention is to provide for a method and an apparatus for measuring the viscosity of very small quantities of highly viscous fluids and for deriving signals thereof.

A specific object of the invention is to provide for a method and an apparatus for affinity viscometry using very small quantities of highly viscous fluids and for deriving signals thereof.

Other objects will in part be obvious and will in part appear hereinafter.

BRIEF SUMMARY OF THE INVENTION

In the accomplishment of these and other objects, the invention provides for a sensor for viscosity measurements in small fluid volumes without fluid consumption, and for methods of a miniaturized sensor suitable for carrying out such measurements, including affinity viscometry.

An important aspect of the invention resides in the securing of closely spaced electrical conductors on a body of silicon or of some other suitable mechanically stable substrate. At least one of the conductors is connected to at least one controlled current source and/or at least one high frequency voltage source, and, within a small measuring zone, at least one of the conductors is separated from the substrate and in at least one sufficiently long section is supported freely in a cantilevered manner and is rigidly anchored or resiliently suspended at predetermined positions and is movable in the measuring zone in consequence of its inherent resiliency. The at least one conductor may thus move reciprocally in the fluid to be analyzed, when subjected to electrostatic attraction or attractive or repulsive magnetic forces. The measuring zone is freely accessible and is located in a small measuring chamber provided with pores or openings for an exchange of material by convection or diffusion. Within the measuring zone, the at least one conductor consists of a very thin resilient material provided with a preferably insulated or passivated surface.

By positioning the measuring zone in a measuring chamber and by connecting it through pores with the medium for the convective or diffusive exchange of material, the influence of movements in the fluid to be analyzed upon the measuring process is reduced or eliminated. Where the measuring chamber is completely enclosed by a dialysis membrane, a diffusion equilibrium relative to the exterior solution will be established within a short period. This may be realized, for instance, by a silicon body provided with a rod-like thin point containing the cantilevered conductor arrangement and positioned within the lumen of a hollow fiber without completely filling the lumen such that the space between the membrane of the hollow fiber and the silicon body is structured as a chamber wherein the measuring zone is contained.

In case the measuring chamber is formed by a semipermeable hollow fiber membrane it may be filled with a sensitive fluid the polymeric components is of which remain enclosed and the viscosity of which depends upon the concentration of the permeable analyte. Hence, the apparatus in accordance with the invention constitutes a sensor operating on the principle of viscometric affinity.

Where the substrate used is a silicon body, it is possible by modern fabrication technologies to integrate circuits for collecting, converting and outputting signals, thereby facilitating the manufacture of a conveniently portable semi-invasive sensor. Given the current state of high frequency technology, the invention also makes possible the development of a completely implantable sensor providing for wireless signal transmission.

In accordance with the method of the invention of measuring viscosity, at least one passivated resiliently movable thin conductor supported in a cantilevered manner within the measuring zone is repulsed and attracted and moved by a sequentially changing magnetic field or by an electrical high frequency signal of sequentially changing amplitude. Where the power is generated by an electrical high frequency field, the use of very high frequencies is advantageous as it substantially neutralizes the effect of the power on the solution in the measuring zone. The rate of the electrically or electromagnetically induced change of position, or of the resilient relaxation of the cantilevered movable conductor into its initial position, is a function of the viscosity of the fluid and may be detected, for instance, by measuring the capacitance or impedance between the moveable conductor and a conductor in the substrate disposed a small distance from the moveable conductor.

Passivated aluminum wire has been found to be a particularly advantageous material for making movable conductors because it can be easily integrated in the silicon body and because of its favorable ratio of electrical conductivity to weight or mass. The utilization of very high frequencies, for instance in the GHz range, is also advantageous for measuring the distance in view of the fact that it makes it possible to measure the capacitance substantially independently of the electric conductivity of the analyzed fluid.

In accordance with the invention, the viscosity-dependent parameter is generally derived by measuring the speed of movement of the cantilevered conductor during or following a change in the electric or magnetic force. In this connection, the viscosity-dependent kinetics of the resilient relaxation following a change in the deflecting force may be quantitatively characterized by the time constant of the resiliency or viscosity or by the initial rate of change of the distance parameter (capacitance, impedance) which depends upon the viscosity and upon the extent of the deflection of the movable conductor. It is also possible to measure the delay or attenuation apparent in the movement of the cantilevered conductor as a change in amplitude at a periodic change of the deflecting force, and it may be advantageous to measure the frequency dependence of this delay or attenuation.

In an alternate embodiment of the invention, at least one moveable cantilevered conductor is positioned in the effective field of a permanent magnet such that the flux lines thereof extend substantially normal to the main directional movement of the conductor.

In a further variant of the invention, the movable conductor constitutes a movable energy conductive loop, hereinafter sometimes referred to as a loop, cantilevered into the measuring zone and positioned above a further loop embedded in the substrate. A current for generating magnetic forces sufficiently strong resiliently to deflect the movable loop is periodically flowing in both loops.

The advantages of the apparatus thus defined, the structure, fabrication and use of which will be described hereinafter in connection with a preferred embodiment, are that it lends itself to miniaturization, to fabrication processes well-known in silicon technology and that it makes possible practicable methods of detecting viscosity-dependent parameters in a small volume and at short intervals.

DESCRIPTION OF THE SEVERAL DRAWINGS

Figure 2:
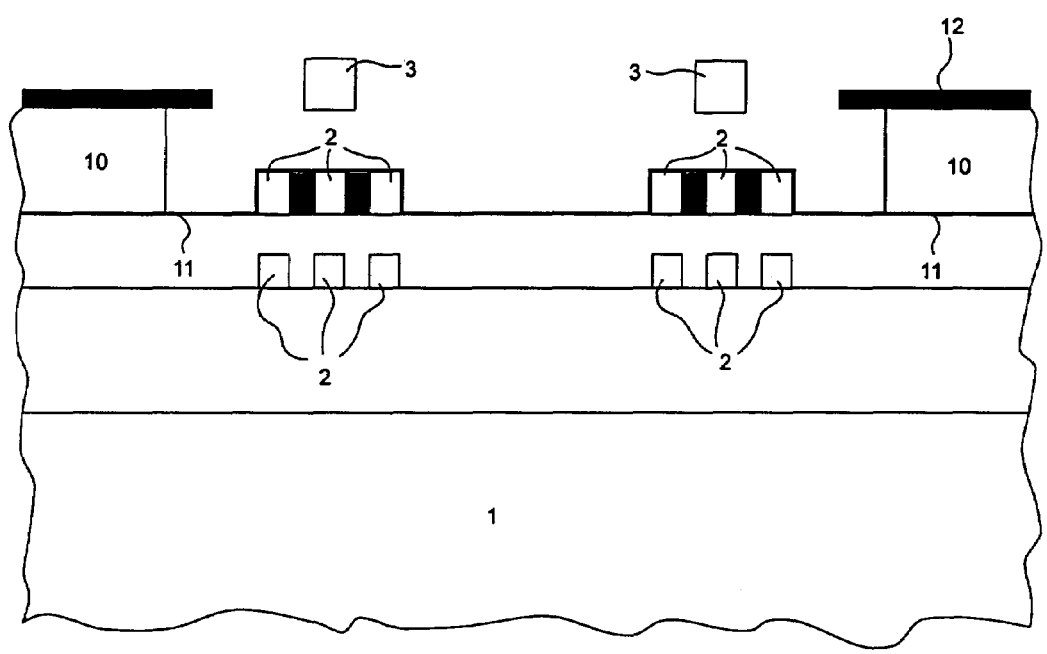

The novel features which are considered to be characteristic of the invention are set forth with particularity in the appended claims. The invention itself, however, in respect of its structure, construction and lay-out as well as manufacturing techniques, together with other objects and advantages thereof, will be best understood from the following description of a preferred embodiment when read in connection with the appended drawings, in which:

FIG. 1 is a schematic top elevational view of an apparatus in accordance with the invention; and FIG. 2 is a sectional view on an enlarged scale along line II-II of FIG. 1.

DETAILED DESCRIPTION OF THE PREFERRED EMBODIMENT

A preferred embodiment of the invention will hereinafter be described with reference to FIG. 1 and FIG. 2. An elongate body or substrate 1 of silicon of substantially square cross section is provided at its right end, as seen in FIG. 1, with a substantially coaxially disposed extension, hereinafter sometimes referred to as a tip, of reduced diameter. By way of example, the length and width of the extension may be about 1 mm and about 300 μm, respectively. The extension supports energy conducting loops made of aluminum, disposed in parallel and connected to sources of energy (not shown). The energy may be direct current and/or high frequency voltage, preferably in the Ghz range. Some of the energy conducting loops, hereinafter referred to as loops, are connected in series and form a flat or loop coil 2 rigidly connected to, or embedded in, the silicon substrate. A further loop 3 made from passivated aluminum and disposed in a measuring zone is extending in a cantilevered fashion over the loop coil 2 at a predetermined spacing therefrom. The loop 3 is mounted at points 4, 4a and 4b for resilient movement relative to the flat coil 2 by torsion wires of the same material as the loop 2, such that the resilient resistance to movement of the loop 3 cantilevered in the measuring zone is chiefly determined by the torsion of elongate wire sections and thus is correspondingly very weak. Accordingly, the movable loop 3 may be easily resiliently deflected relative to the body by magnetic forces induced by electric currents flowing in opposite directions in the flat coil and in the movable loop 3. When the current is turned off the movable loop 3 returns to its initial or rest position as a result of the restoring force inherent in its resiliency at a rate dependent upon the viscosity of the fluid to be analyzed. The viscosity-dependent initial velocity of this movement or the viscosity-dependent time constant of the resilient relaxation is established indirectly by measuring the change over time of the high frequency capacitance between the movable loop 3 and the flat coil 2 rigidly mounted on the surface of the silicon substrate 1. To this end, the measuring frequency is selected sufficiently high to prevent the conductivity of the analyzed fluid from affecting the capacitance measurement. The active and passive microelectronic circuit components (circuit block 5) required for generating the high frequency voltage necessary for measuring the capacitance, for generating signals representative of the capacitance and for converting or amplifying signals are arranged on the silicon substrate 1. Logic circuits (circuit block 6) for controlling the direct currents flowing in the loops 2 and 3 are also provided on the substrate 1.

Preferably, the silicon extension or tip supporting the movable loop 3 and the flat coil 2 are housed in a dialysis hollow fiber segment 7 having a molecular weight cut-off of about 10 kDa, the hollow fiber segment 7 containing the lyophilized components of a fluid sensitive to glucose (ConA and dextran, Ballerstädt, R., Ehwald, R. German patent specification 44 46 695). The fiber segment 7 preferably is made from a semi-permeable membrane, and the movable loop 3 is positioned in the small space between the semi-permeable membrane 7 and the silicon substrate 1. At sections 8, the enclosed volume or dialysis chamber is closed to, or hermetically sealed from, the environment by a seal 8 of suitable polymeric material 8. The lay-out of the chamber is such that the distance between any point in the chamber and the permeable portion of the dialysis membrane does not exceed 0.3 mm. The diffusion equilibrium between glucose in the chamber and glucose outside of the chamber will thus be established in the chamber within two minutes.

Following introduction of the silicon extension and dialysis chamber into a degassed buffer solution or into a body fluid, the lyophilized dextran and ConA molecules of the sensitive fluid will be dissolved in the lumen of the thus formed dialysis chamber so that a sensitive fluid will be present in the chamber. The viscosity of the enclosed sensitive fluid is determined at a constant temperature and a constant pH value by the concentration of diffusible sugars and glycosides, since in blood or tissue fluid glucose is the only substance which affects the viscosity of the sensitive fluid. Depending upon individual requirements, the signal transmission from the sensor chip, i.e., the tip or extension, described above to a signal evaluation circuit 9 and the supply of energy to the sensor chip my be wired or wireless.

As regards the fabrication of the apparatus described, the structuring of the measuring zone and the movable loop 3 is significant. In accordance with the invention, the movable loop 3 is fabricated only after formation of all active and passive components of the integrated circuit of the viscosity sensor has been completed, by applying an additional photo lithographically structured resist mask prior to separating the sensor chips produced on a semiconductor substrate (wafer). The mask serves, by a localized isotropic insulator etching process, to undercut and completely separate from the insulating support, the portion of the conductor plane which in the completed sensor constitutes the resiliently moveable loop 3.

Advantageously, the intermediate insulator between the uppermost and the underlying conductive layer consists of at least two layers of different chemical composition and one of the lower partial layers of the intermediate insulator is not affected by the etching agent used for the isotropic undercutting of the uppermost conductive layer.

This may be accomplished by the upper partial layer 10 of the intermediate insulator consisting of silicon dioxide or silicate glass and a lower partial layer 11 consisting of $Si_3N_4$. The windows in the passivation layer 12 which also consist of $Si_3N_4$, which have been structured with the above-mentioned additional resist mask prior to the isotropic undercutting, serve as an etching mask.

Following separation of the chips they are mechanically processed for fabricating the sensor tip or extension. Thereafter, the dialysis hollow fiber segment 7 containing the active components of the sensor fluid is mounted over the extension.

What is claimed is:

1. An apparatus for measuring viscosity of a medium with a micromechanical measuring facility and electronic systems for measuring, transducing, and analyzing signals, with the following features:
   a measuring zone integrated on a mechanically stable substrate is freely accessible or enclosed within a measuring chamber with pores or openings for diffusive or convective mass transport, the measuring zone containing two or more closely spaced conductors of which at least one is connected to a controllable current source or HF voltage source and of which at least one is completely or partially cantilevered from a suspension into the measuring zone, the position of the cantilevered conductor(s) being defined within the measuring zone by the resiliency of the suspension or their/its inherent resiliency and by voltage-dependent, or current-dependent electrical or magnetic attraction, or repelling forces, which can be changed by said HF voltage source or current source, and the measuring zone containing an integrated measuring device for detecting a viscosity-dependent change in position of the conductor(s) in response to changes of said attraction or repelling forces.

2. The apparatus of claim 1, wherein the substrate comprises a semiconductor material and contains integrated circuits for detecting the position or change in position of the cantilevered conductor(s), and/or for the signal transduction, and/or the signal export, and/or for the controllable current or HF voltage sources.

3. The apparatus of claim 1, wherein an integrated loop or flat coil and the cantilevered conductor(s) are arranged on the substrate at the measuring zone, the cantilevered conductor(s) being suspended from the substrate at two or more points within the measuring zone.

4. The apparatus of claim 1, wherein the substrate is formed as a bar-shaped, thin tip at the measuring zone.

5. The apparatus of claim 4, wherein the measuring zone is separated from the medium to be analyzed by a dialysis membrane forming a measuring chamber filled with a macromolecular sensitive fluid, the components of which cannot penetrate the dialysis membrane and the viscosity of which is determined by reversible affinity bonds between polymer substances and can be changed by the concentration of one or more analyte molecules for which the dialysis membrane is permeable, wherein the maximum spacing between the sensitive fluid volume confined by the dialysis membrane and the substrate is 0.5 mm.

6. The apparatus of claim 5, wherein the bar-shaped, thin tip with the measuring zone is positioned in and partially fills the lumen of a dialysis hollow fiber for forming a measuring chamber in the region between hollow fiber membrane and substrate.

7. The apparatus of claim 6, wherein the cantilevered conductor(s) consist(s) of thin metal wires and wherein, the resilient resistance of the conductor(s) against the field-induced force is mainly based on the torsion of said wires.

8. The apparatus of claim 7, wherein the cantilevered conductor(s) is/are arranged in the field of a permanent magnet such that this field is directed perpendicularly to the conductor(s) and to their/its main direction of movement and wherein the conductor(s) is/are connected to a controllable current source.

9. A method of measuring viscosity with a device according to claim 8, wherein the change in the position of the cantilevered conductor(s) relative to the substrate or another conductor is induced by a change of the electrical HF field or of the magnetic field intensity and the viscosity dependent velocity or extent of change in position induced by a preferably high frequency capacity or impedance measurement or by a frequency-shift of an HF-oscillator.

10. The method of measuring viscosity of claim 9, wherein the viscosity-dependent amplitude of the measured change in position of the cantilevered conductor(s) is evaluated at a suitable modulation or switching frequency of the HF field affecting the conductor(s) or of the current flowing in the conductor(s) or as a function of the modulation or switching frequency.

11. The method of measuring viscosity of claim 9, wherein the strength or direction of the magnetic force or the strength of the electrostatic force acting on the cantilevered conductor(s) is/are abruptly changed by the control of the current- or HF voltage source, and subsequently, the viscosity-dependent change in position of the is/are measured as a function of time.

12. A method of making a device for measuring viscosity according to claim 8, wherein after completion of all active and passive components of the viscosity measuring device on a suitable semiconductor substrate, including the integrated conductors, an additional photolithographically structured resist mask is applied for a localized isotropic insulation etching process on the parts of the uppermost conductor layer for forming the cantilevered conductors and wherein the parts of the uppermost conductor layer are undercut by etching and completely separated from corresponding sections of an insulating base by the localized isotropic insulation etching process.

13. The method of claim 12, wherein a layer intermediate the uppermost conductor layer and a lower conductor is dielectric and consists of at least two layers of different chemical compounds, and wherein the lower part of the intermediate layer is immune from the etching process for the isotropic undercutting of the upper conductor path.

14. The method of claim 13, wherein the upper part of the intermediate layer consists of silicon dioxide or silicate glass and one of the lower partial layers consists of $Si_3N_4$.

15. An apparatus for measuring the viscosity of a fluid, comprising:
    a substantially rigid support;
    an extension protruding from the support and provided with a first conductive path;
    a cantilever member comprising a second conductive path extending over the first conductive path and resiliently biased to a first position spaced therefrom;
    means for cyclically energizing at least one of the first and second conductive paths for moving the cantilever member to a second position; and
    means for detecting the rate of return of the cantilever member to its first position to derive a value representative of the viscosity.

16. The apparatus of claim 15, wherein the length and width of the extension are about 1 mm and 300 μm, respectively.

17. The apparatus of claim 16, wherein the extension and the cantilever member are mounted in a chamber formed by a membrane of predetermined permeability.

18. The apparatus of claim 17, wherein the membrane is a dialysis membrane and wherein the layout of the chamber is such that the distance between any point in the chamber and a permeable portion of the membrane does not exceed 0.3 mm.

19. The apparatus of claim 18, wherein the dialysis membrane has a molecular weight cut-off of about 10 kDa.

20. The apparatus of claim 19, wherein the chamber contains lyophized components of a fluid sensitive to glucose.

21. The apparatus of claim 15, wherein the at least one of first and second conductive paths is adapted to be energized by direct current.

22. The apparatus of claim 15, wherein the at least one of first and second conductive paths is adapted to be energized by high frequency voltage.

23. The apparatus of claim 22, wherein the high frequency voltage is in the Ghz range.

24. A method of measuring the viscosity of a fluid, comprising the steps of:
    providing a substantially rigid member with a first conductive path therein;
    providing a resiliently flexible member having a second conductive path therein biased into a first position spaced from the first conductive path;
    subjecting the rigid and flexible members to the fluid;

energizing at least one of the first and second conductive paths to move the flexible member to a second position; and measuring the rate of movement of the flexible member to derive therefrom a value representative of the viscosity.

25. The method of claim 24, wherein the at least one conductive path is energized by high frequency voltage and wherein the rate of movement is measured by the capacitance between the first and second conductive paths.

26. The method of claim 24, wherein the at least one conductive path is energized by direct current and wherein the rate of movement is measured by rate of relaxation of the resilient member.

27. The method of claim 24, wherein the rigid and resiliently flexible members are disposed in a measuring chamber formed by a membrane of predetermined permeability and wherein the chamber further contains a fluid sensitive to the fluid for measuring the viscosity thereof by affinity.

28. A method of fabricating an apparatus for measuring the viscosity of a fluid, comprising an elongate rigid member extending from a substrate of a semiconductor material for supporting a first conductive path and a second member supporting a second conductive path and mounted for movements relative to the first member, wherein the second member is formed by depositing on the parts of the substrate provided with the second conductive path an additional photolithographic resist mask for undercutting by localized isotropic insulator etching.

29. The method of claim 28, wherein an intermediate layer comprising at least two superposed layers of different chemical compounds is provided between the first and second conductive paths and wherein the etching step is performed on an upper one of the layers.

30. The method of claim 29, wherein the etching step is performed with an etching agent removing layers of one of silicon dioxide and silicate glass and immune to lower layers of $Si_3N_4$.

* * * * *